United States Patent
Stevens et al.

[11] Patent Number: 6,017,555
[45] Date of Patent: Jan. 25, 2000

[54] PROCESS FOR MAKING L-LYSINE FEED SUPPLEMENT

[75] Inventors: Joseph Michael Stevens, Monticello; Thomas P. Binder, Decatur, both of Ill.

[73] Assignee: Archer Daniels Midland Company, Decatur, Ill.

[21] Appl. No.: 09/098,948

[22] Filed: Jun. 17, 1998

Related U.S. Application Data

[63] Continuation-in-part of application No. 08/991,145, Dec. 16, 1997.

[51] Int. Cl.[7] .................................................... A23K 1/18
[52] U.S. Cl. .......................... 424/438; 424/489; 426/2; 426/53; 435/115; 562/562
[58] Field of Search ..................... 424/438, 489; 426/2, 53; 435/115; 562/562

[56] References Cited

U.S. PATENT DOCUMENTS

| | | | |
|---|---|---|---|
| 3,089,824 | 5/1963 | Wurster | 167/82 |
| 4,181,708 | 1/1980 | Dannelly | 424/482 |
| 4,327,118 | 4/1982 | Georgen et al. | 426/656 |
| 4,996,067 | 2/1991 | Kobayashi et al. | 426/96 |
| 5,133,976 | 7/1992 | Rouy | 426/2 |
| 5,300,318 | 4/1994 | Pierre et al. | 427/212 |
| 5,431,933 | 7/1995 | Binder et al. | 426/60 |
| 5,622,710 | 4/1997 | Binder et al. | 424/438 |

FOREIGN PATENT DOCUMENTS

| | | |
|---|---|---|
| 91460051 | 6/1992 | European Pat. Off. . |
| WO 95/23129 | 8/1995 | WIPO . |

OTHER PUBLICATIONS

Saksaoka et al, Coated feed additives for ruminants, CA: 110: 172054b, Dec. 1988.

*Primary Examiner*—Porfirio Nazario-Gonzalez
*Assistant Examiner*—Taylor Victor Oh
*Attorney, Agent, or Firm*—J. Warren Whitesel; Laff, Whitesel & Saret, Ltd.

[57] ABSTRACT

A process produces an L-Lysine feed supplement with a final L-Lysine purity in the range theoretically between about 35% and 80%, measured as a percent of free-base per kg, and more preferably between about 50% and 80% L-Lysine. The process comprises adding a material containing L-Lysine to an L-Lysine fermentation broth or a fraction of an L-Lysine fermentation broth. The added material being an amount which brings a final L-Lysine feed supplement with an L-Lysine purity into a range theoretically between about 35% and 80%, measured as a percent of free-base per kg, and more preferably between about 50% and 80% L-Lysine. The fraction of L-Lysine fermentation broth is obtained by any suitable separating means such as ultrafiltration or centrifugation. The process also comprises a drying step which may involve any suitable drying means such as a spray granulator, spray dryer, tray dryer, drum dryer, rotary dryer, and tunnel dryer.

24 Claims, 7 Drawing Sheets

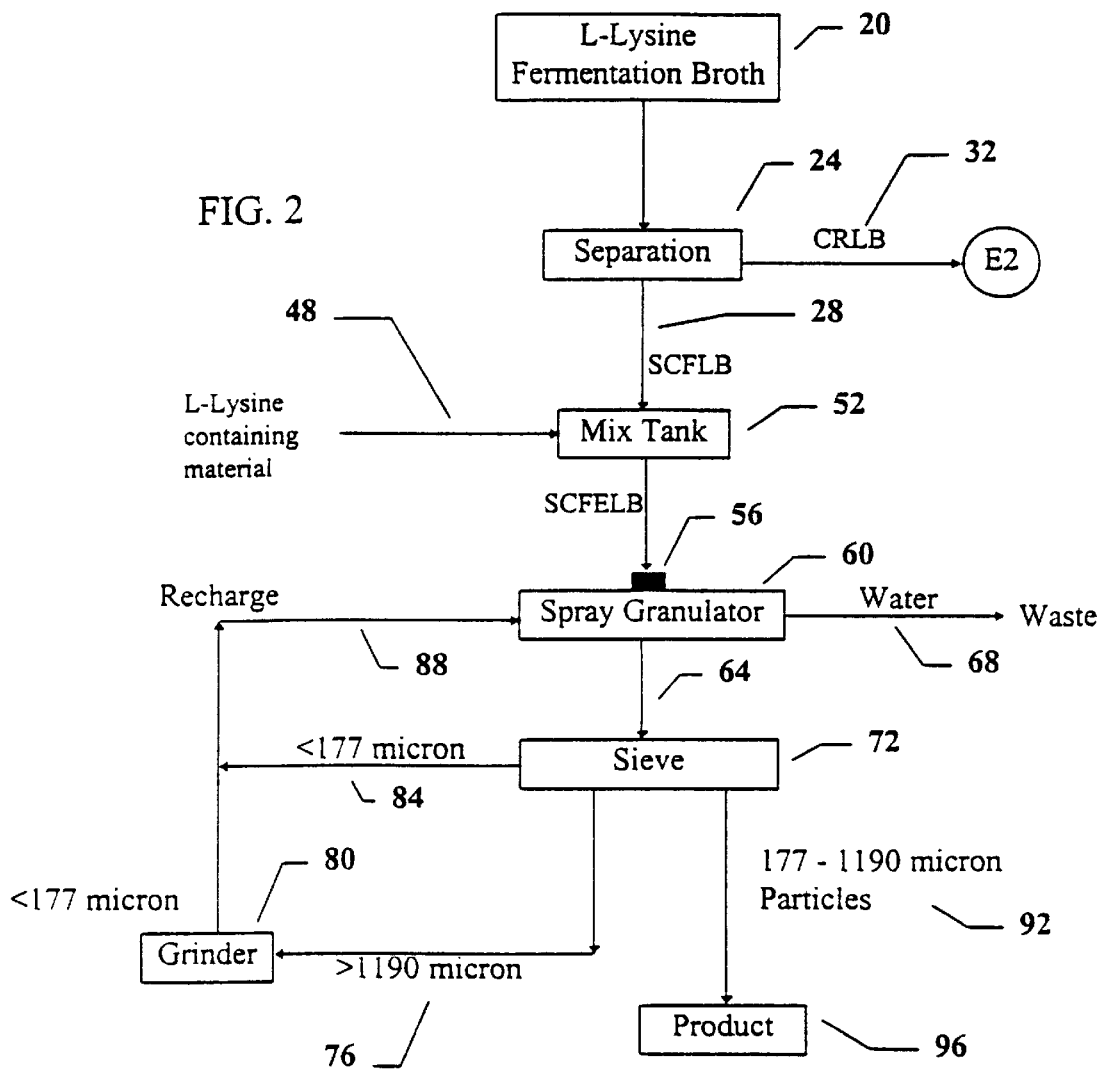

6,017,555

PROCESS FOR MAKING L-LYSINE FEED SUPPLEMENT

This application is a continuation-in-part of copending application Ser. No. 08/991,145 filed on Dec. 16, 1997.

The invention relates to processes for producing an L-Lysine feed supplement derived from L-Lysine fermentation broth, and more particularly, to producing an L-Lysine feed supplement in which the L-Lysine content is not solely dependent on the initial L-Lysine concentration in the L-Lysine fermentation broth.

BACKGROUND OF THE INVENTION

Reference is made to copending parent application Ser. No. 08/991,145 filed on Dec. 16, 1997, the subject matter of which is incorporated herein by this reference thereto.

Lysine is an amino acid used extensively in the animal feed industry, the major form of which is L-LysineHCl (L-Lysine monohydrochloride). For many years, an L-LysineHCl solid has been produced by a process of fermentation, purification, crystallization and drying. After fermentation, the resulting broth may be rendered cell free by filtration or centrifugation. After filtration, the L-Lysine may be recovered from the fermentation broth by an ion exchange step, that produces a liquid which is substantially L-Lysine free base. This solution may then be concentrated by evaporation.

Hydrochloric acid was usually added to the concentrated L-Lysine free base to form L-LysineHCl. This concentrated L-LysineHCl solution was crystallized to produce a product in the form of L-LysineHCl dihydrate (L-LysineHCl:2H$_2$O). This crystallized solid was thereafter dried to have less than one percent moisture.

This conventional product may have shortcomings. For example, it is dusty. During the handling of the product, the dust results in a loss of valuable material and sometimes causes an incomplete formulation. Also, human working conditions are made less healthful and more difficult as a result of the dust contributed by the L-LysineHCl. Sometimes the product develops lumps during storage which are difficult to break up at the time of end use. In addition, the extensive use of an ion exchange makes this process expensive.

Direct spray drying of an L-Lysine fermentation broth avoids the extensive purification steps associated with the L-Lysine hydrochloride process, in particular the use of an expensive ion-exchange. However, consistent L-Lysine concentration in the final dry product is difficult to achieve because the L-Lysine concentration in a fermentation broth can vary considerably. Also, the dry product may be dusty and difficult to use.

U.S. Pat. No. 5,431,933 describes a process for the production of an amino acid feed supplement which "still contains most of the solids content of the fermentation broth." The production of a fermentation broth at the industrial scale with 40 to 50 percent L-Lysine content is very difficult to achieve from an operational standpoint. Malfunctioning fermenters, contamination, power outages, and operator error are quite common and are likely to lead to fermentation material that is less than about 40 percent L-Lysine and therefore of little value. This difficulty is compounded by the impurities associated with the media components, many of which are unrefined and vary in solids content and nutrient value from lot to lot. To avoid variance in media, fermentation is constrained to specific and expensive media. These considerations may lead to an increase in operational input which is necessary to make a 40 to 50 percent L-Lysine product, leading to high manufacturing costs which may be prohibitive.

A process in which a non-dusty granular animal feed product is formed is described in U.S. Pat. No. 5,622,710. First, the fermentation broth is spray dried to produce particles which may include biomass. In the second step, the particles are converted into pellets by means of costly high shear mixing equipment.

European Application Number 91460051.5 describes a method of making a granulated L-Lysine dust free, free-flowing, L-LysineHCl granular product from a liquid solution or slurry by a spray granulation process. In one embodiment of the invention, elements from a fermentation broth containing L-Lysine is ion exchanged to produce a purer L-Lysine solution. Hydrochloric acid is then added to the purer L-Lysine solution to make L-LysineHCl which is then sprayed onto an agitated drying bed of L-Lysine particulates. The particles of L-LysineHCl are then recovered once they reach a predetermined size.

International Publication Number WO/95/23129 describes the production of non-stoichiometric salt of L-Lysine in granular form. This publication teaches the production of non-stoichiometric salts of L-Lysine wherein the amount of L-Lysine content in the final product is adjustable. While the requirement for hydrochloric acid is reduced, other materials are called for such as calcium hydroxide, sulfuric acid or phosphoric acid. In addition, the fermentation broth containing the L-Lysine is extensively ion-exchanged.

U.S. Pat. No. 3,089,824 describes the use of a fluidized bed for the manufacture of compressed tablets for medical use. The process comprises (1) forming a suspension of particles in air, (2) enabling the particles to be built up with granulating material, and (3) coating the resulting granules with a lubricant. In one aspect of this invention, the granulating material is atomized and sprayed into the air stream of a fluidized bed of inert particles such as sucrose. The inert particles act as nuclei for the granulation process. The resulting granules are coated with a lubricant.

The copending parent application (Ser. No. 08/991,145 filed on Dec. 16, 1997) describes an extremely useful process for making a substantially non-dusty granular L-Lysine product in which the concentration of L-Lysine in the final product is controlled by the addition of material containing L-Lysine, which is added prior to an agglomeration step (i.e. spray granulation step). There are occasions where a non-granular L-Lysine feed supplement with an adjustable amount of L-Lysine purity is desirable on economic grounds.

As useful as the copending parent application is, the process describes an ultrafiltration step to provide a substantially cell free L-Lysine broth and a cell rich L-Lysine broth in the form of a permeate and a retentate respectively. The cell rich L-Lysine broth is abandoned as waste. The ultrafiltration step adds considerably to plant costs.

Care should be taken either to use or to properly dispose of the cell rich L-Lysine broth. The cell rich L-Lysine broth is frequently treated as a waste by-product and requires primary and secondary waste water treatments. If the cell rich L-Lysine broth is released as untreated sewage this may have a deleterious impact on the environment.

SUMMARY OF THE INVENTION

Accordingly, an object of this invention is to provide a more flexible process to produce a L-Lysine product in which the concentration of L-Lysine in the final product is controllable. Another object is to provide a process which employs cell rich L-Lysine broth to produce a L-Lysine product in which the concentration of L-Lysine in the final product is controllable. Yet another object is to provide a non-granular L-Lysine feed supplement with an adjustable amount of L-Lysine wherein the spray granulation step is replaced with alternative methods of drying such as spray drying, drum drying, rotary drying, tray drying, and tunnel drying.

BRIEF DESCRIPTION OF THE DRAWINGS

The above mentioned and other features of this invention and the manner of obtaining them will become more apparent, and the invention itself will be best understood by reference to the following description of the invention taken in conjunction with the accompanying drawings, in which:

FIG. 2 is a flow chart, showing the principal steps in a process for producing an L-Lysine feed supplement in which the ultrafiltration step is optional and the water removal step is excluded;

BRIEF DESCRIPTION OF PREFERRED EMBODIMENTS

Figure 1:
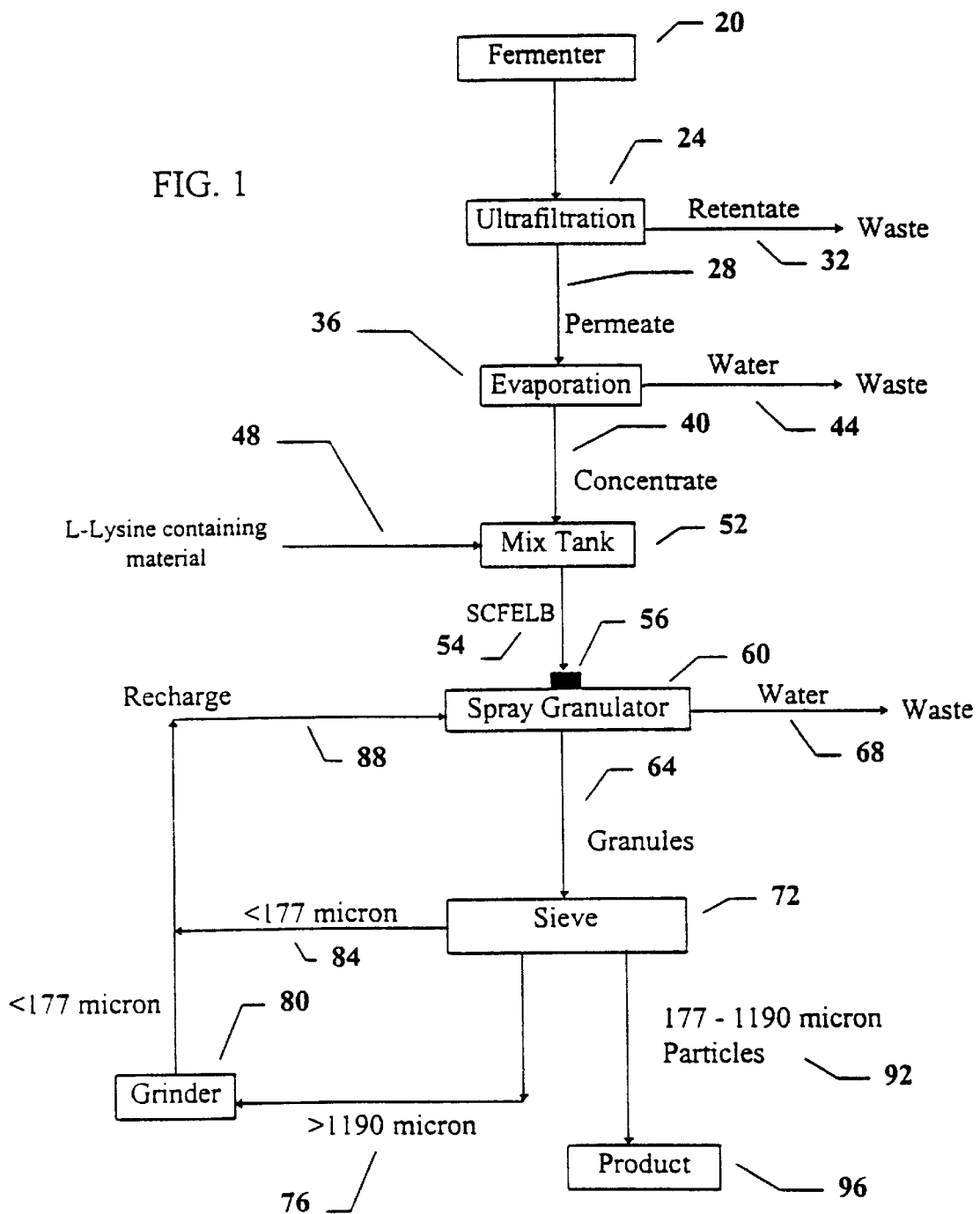
FIG. 1 is a flow chart, showing the principal steps in a process for producing a substantially dust free, free flowing, granular L-Lysine in the manner described in the copending application (Ser. No.: 08/991,145), that description being incorporated herein by this reference thereto.

The copending application (Ser. No.: 08/991,145), describes principal steps in a process for producing a substantially dust free, free flowing, granular L-Lysine (FIG. 1) with an adjustable amount of L-Lysine purity in a range between about 35% and 80% L-Lysine, measured as a percent of free-base per kg. These steps comprise: (a) ultrafiltration of an L-Lysine fermentation broth to provide a substantially cell free L-Lysine permeate 28; (b) removing water from the L-Lysine permeate of step (a) to provide a substantially cell free concentrated L-Lysine broth 40; (c) adding a material containing L-Lysine to the L-Lysine broth of step (b) to provide a substantially cell free enriched L-Lysine broth (SCFELB 54); and (d) agglomerating the L-Lysine broth of step (c) to provide a feed supplement in the form of a substantially dust free, free flowing, granular L-Lysine product at 96.

The principle steps of an inventive process (FIG. 2) described herein produces an L-Lysine feed supplement with a final L-Lysine purity in the range theoretically between about 35% and 80%, measured as a percent of free-base per kg, and more preferably between about 50% and 80% L-Lysine. The inventive process in which the ultrafiltration step can be replaced with a centrifugation step and the water removal step is excluded, comprises: (a) separating, by any suitable means such as centrifugation, an L-Lysine fermentation broth into two fractions: a cell rich L-Lysine broth (CRLB 32) and a substantially cell free L-Lysine broth (SCFLB 28); (b) adding a material containing L-Lysine at 48 to the L-Lysine broth of step (a) in a mix tank 52 to provide a substantially cell free enriched L-Lysine broth (SCFELB), the added material is an amount which brings a final L-Lysine feed supplement with a L-Lysine purity to be in a range between about 35% and 80% L-Lysine, measured as a percent of free-base per kg; (c) agglomerating the L-Lysine broth of step (b) by using a spray granulator 60 to provide particles of L-Lysine; and (d) sieving the particles of step (c) to provide the final L-Lysine feed supplement 96.

Alternatively, the substantially cell free enriched L-Lysine broth of step (ii) may be spray dried (60 in FIG. 2A) to provide an L-Lysine feed supplement 97. An L-Lysine feed supplement 96 may also be produced by tunnel drying, drum drying, rotary drying or tray drying the substantially cell free enriched L-Lysine broth (62 in FIG. 2A). If a tunnel drying, drum drying, rotary drying or tray drying means are employed, excess water is preferably removed (63 in FIG. 2A), and preferably removed by evaporation.

Figure 3:
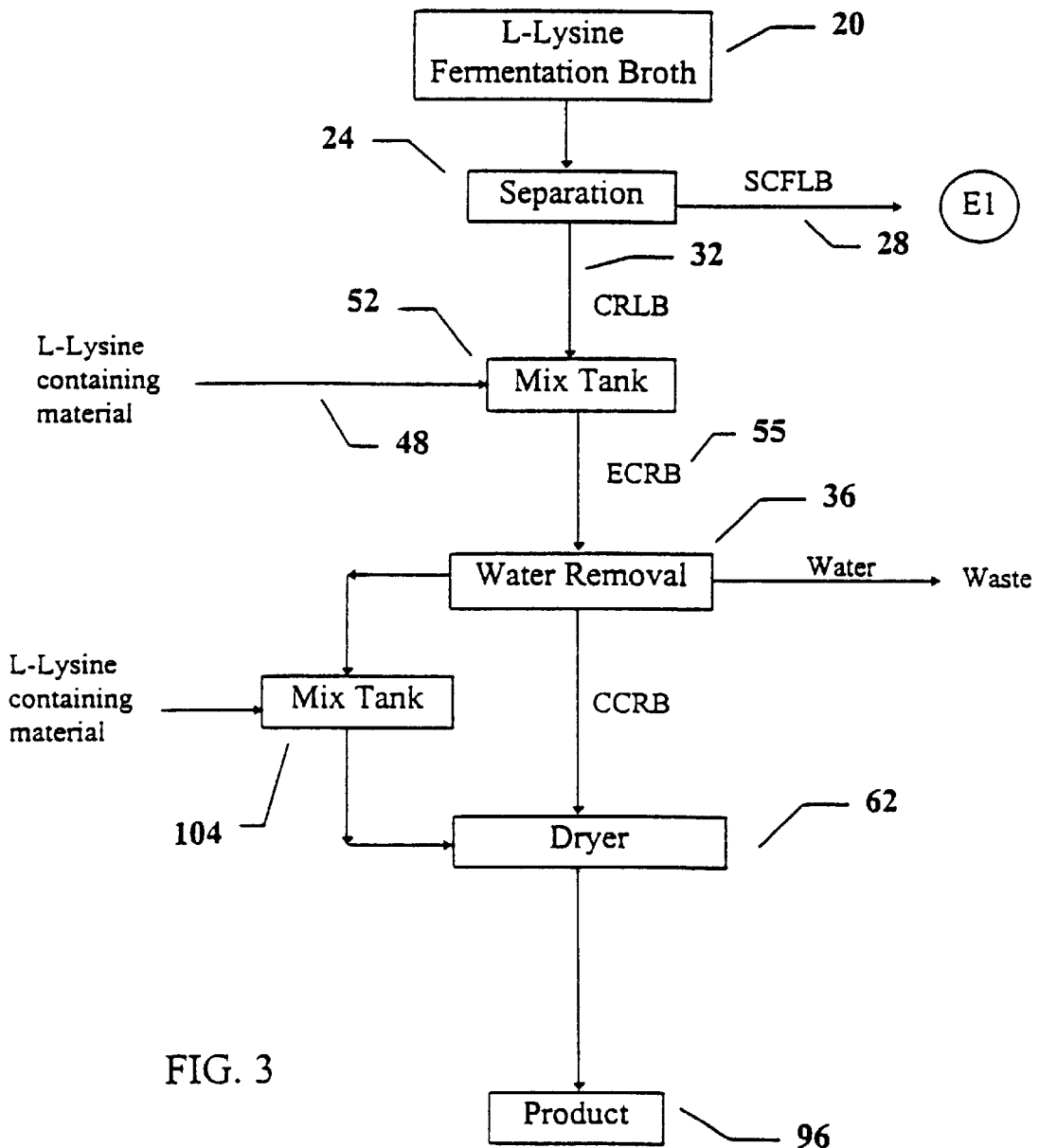
FIG. 3 is a flow chart, showing the principal steps in a process for producing an L-Lysine feed supplement in which there are two entry points for an L-Lysine containing material.
Figure 3A:
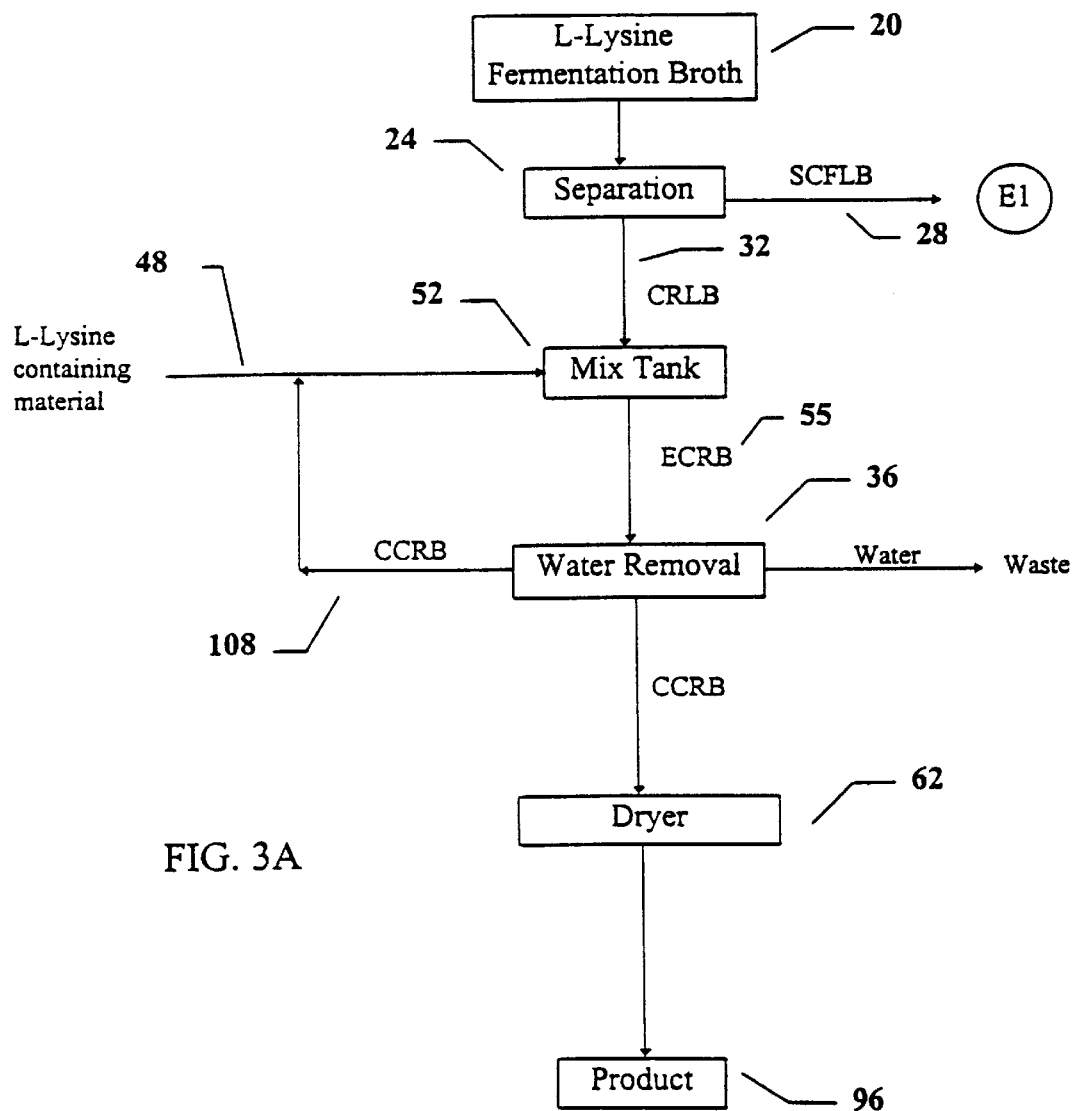
FIG. 3A is a flow chart, showing the principal steps in a process for producing an L-Lysine feed supplement in which a concentrated cell rich broth may be recycled for the addition of more L-Lysine containing material.

The principle steps of one aspect of the inventive process (FIG. 3) described herein produces an L-Lysine feed supplement with a final L-Lysine purity in the range theoretically between about 35% and 80%, measured as a percent of free-base per kg, and more preferably between about 50% and 80% L-Lysine. The principal steps comprises: (a) an L-Lysine fermentation broth separated into two fractions to produce a substantially cell free L-Lysine broth (SCFLB 28) and a cell rich L-Lysine broth (CRLB 32); (b) adjusting the L-Lysine purity of the cell rich L-Lysine broth of step (a) to provide an enriched cell rich broth 52; (c) removing water from the enriched cell rich broth of step (b) to produce a concentrated cell rich broth 36; and (d) either drying the concentrated cell rich broth of step (c) to provide an L-Lysine feed supplement (96) or blending the concentrated cell rich broth of step (c) with more L-Lysine containing material at 104 and then drying to provide an L-Lysine feed supplement at 96. The concentrated cell rich broth may be blended with more L-Lysine containing material on a batch or semi-batch basis as depicted in FIG. 3a.

The principle steps in yet another inventive process (FIG. 4) for producing an L-Lysine feed supplement with an adjustable amount of L-Lysine purity comprises: (a) adjusting the L-Lysine purity of an L-Lysine fermentation broth to provide an enriched L-Lysine fermentation broth; and (b) converting the enriched L-Lysine fermentation broth of step (a) into an L-Lysine feed supplement by either spray granulation, spray drying, tunnel drying, tray drying, rotary drying or drum drying.

Figure 4:
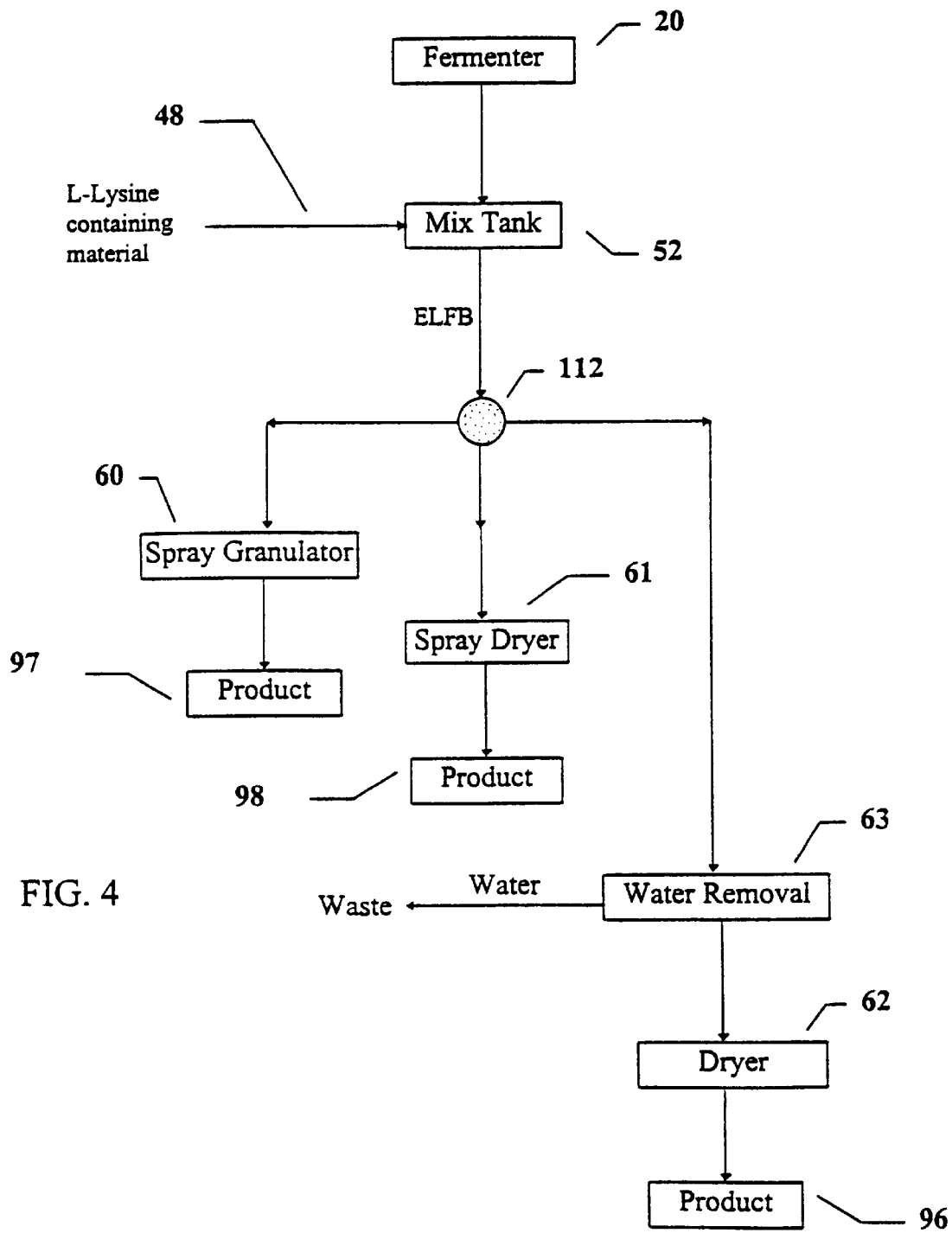
FIG. 4 is a flow chart, showing the principal steps in a process for producing an L-Lysine feed supplement in which an L-Lysine containing material is added to an L-Lysine fermentation broth.
Figure 5:
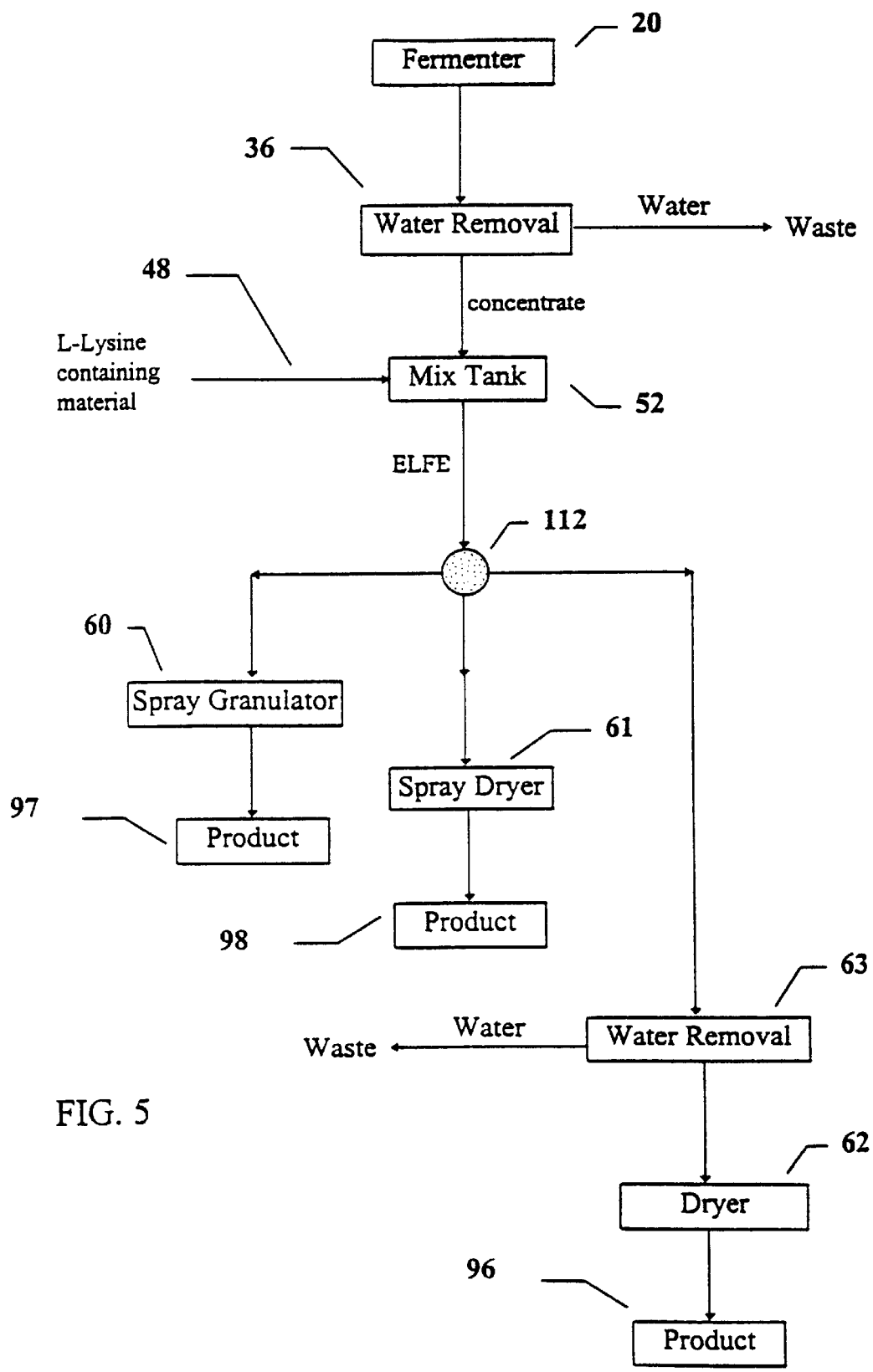
FIG. 5 is a flow chart, showing the principal steps in a process for producing an L-Lysine feed supplement in which an L-Lysine containing material is added to a concentrated L-Lysine broth.

The principle steps in yet another inventive process (FIG. 5) for producing an L-Lysine feed supplement in a similar manner to that described by FIG. 4 with the optional step of removing water, preferably by evaporation, from the L-Lysine fermentation broth at 36 in order to provide a concentrated L-Lysine broth with between about 30% and 70% solids by weight. An L-Lysine containing material is added to the concentrated L-Lysine broth at 48 to provide an enriched L-Lysine fermentation broth. The enriched L-Lysine fermentation broth may be spray granulated at 60;

spray dried at 61; and spray dried, spray granulated, tunnel dried, tray dried, or drum dried at 62 to provide an L-Lysine feed supplement with a final L-Lysine purity in the range theoretically between about 35% and 80% L-Lysine, measured as a percent of free-base per kg, and and more preferably between about 50% and 80% L-Lysine.

DETAILED DESCRIPTION OF PREFERRED EMBODIMENTS

For convenience of expression, the term "dryer" will hereafter be used to describe any suitable drying means such as a spray dryer, drum dryer, tunnel dryer, rotary dryer, tray dryer, and spray granulator. In addition, the term "spray granulator" will hereafter be used to describe a "fluidized bed of particulates".

The terms "spray granulation", "spray granulation step", and "agglomeration" will hereafter be regarded as equivalent terms.

The terms "rentenate" and "cell rich L-Lysine broth" will hereafter be regarded as equivalent terms.

The term "separation" will hearafter be used to describe the separating of an L-Lysine fermentation broth into two fractions: a cell rich L-Lysine broth and a substantially cell free L-Lysine broth. Any suitable separating means or combination of separating means may be used. Separation may be achieved by means of filtration (e.g. ultra- and microfiltration), and mechanical methods such as centrifugation and decanting.

The term "ultrafiltration" will hereafter be used to describe the use of an ultrafilter to filter cells from an L-Lysine fermentation broth to provide a substantially cell free L-Lysine broth and a cell rich L-Lysine broth. The ultrafilter used to remove the cells, has a molecular weight cutoff between about 10,000 Dalton and 500,000 Dalton, preferably about 500,000 Dalton.

The terms "evaporation" and "evaporated" will hereafter be used to describe the removal of water by evaporation, which is carried out in the approximate temperature range of between 140° F. and 214° F., preferably between 145° F. and 155° F., with a pressure between 2.9 psia and 11 psia (vacuum), preferably 2.9 psia to 4 psia.

The terms "material containing L-Lysine" and "L-Lysine containing material" will hereafter be regarded as equivalent terms.

The terms "L-Lysine hydrochloride" and "Lysine HCL" will hereafter be regarded as equivalent terms.

The terms "L-Lysine sulfate" and "Lysine $H_2SO_4$" will hereafter be regarded as equivalent terms.

The terms "neutralized L-Lysine free-base", "neutralized L-Lysine", "nfree-base" and "neutralized lysine" will hereafter be regarded as equivalent terms.

The terms "free-base form of L-Lysine" and "L-Lysine free-base" will hereafter be regarded as equivalent terms.

The term "neutralized L-Lysine free-base" will hereafter be used to describe a material containing L-Lysine free-base which has been neutralized using counter-ions such as $Cl^-$ and $SO_4^{2-}$. Neutralized L-Lysine free-base is obtained by reacting at least a stoichiometric amount of an acid such as hydrochloric (HCl) or sulphuric acid ($H_2SO_4$) with L-Lysine free-base.

The term "material containing L-Lysine" will hereafter be used to describe at least one suitable L-Lysine containing material used alone or combination with at least one other suitable L-Lysine containing material. Examples of suitable L-Lysine containing materials are L-Lysine hydrochloride, L-Lysine sulfate, and neutralized L-Lysine.

The term "final L-Lysine feed supplement" will hereafter be used to describe a final product supplement with an L-Lysine purity within a range between about 35% and 80% L-Lysine, measured as a percent of free-base per kg. In addition, the term "final L-Lysine feed supplement" will hereafter be understood to mean a final product in which the L-Lysine in the final product is present in its neutralized form.

While one aspect of this invention is the harvesting and processing of L-Lysine base from fermentation broth, the composition and nature of the fermentation medium may vary. For example, any suitable high L-Lysine producing organism taken from the genus Corynebacterium or Brevibacterium may be used to inoculate the fermentation medium. Prior to inoculation with the L-Lysine producing bacterium, the fermentation medium may have the following composition:

| Material | Amount (g/l) |
| --- | --- |
| Soy Hydrolysate | 20.0 |
| Ammonium Sulfate | 20.0 |
| Urea | 3.0 |
| Monopotassium Phosphate | 1.0 |
| Magnesium Sulfate heptahydrate | 0.5 |
| Manganese Sulfate | 0.002 |
| Biotin | 0.0001 |
| Thiamine Hydrochioride | 0.0001 |
| Glucose | 30.0 |

The pH is adjusted and maintained at approximately 7.2 with ammonium hydroxide The temperature is maintained at about 32° C. The feed is Glucose:$(NH_4)_2SO_4$ with the glucose concentration maintained at about 10 g/l The fermentation medium can be inoculated into the fermentation vessel by using standard microbiological practices which are known to those skilled in the microbiology art. The fermentation vessel should be equipped with a stirrer, a ventilation system, and a temperature control device to maintain the fermentation at about 30° C. and preferably at 32° C. The fermentation is carried out until the L-Lysine base concentration is about 92 g/l (grams per liter) and the total dry solids is about 218 g/l. Aseptic techniques should be observed throughout the fermentation process to avoid a contamination of the fermentation broth with non-L-Lysine producing organisms.

In keeping with a first embodiment that is described in the copending parent application, (FIG. 1), the process produces an L-Lysine feed supplement in the form of a substantially dust free, free flowing, granular L-Lysine from fermentation broth.

(i) An L-Lysine containing fermentation broth in fermenter 20 is separated into two fractions by an ultrafiltration means at 24 to remove cells in order to produce a substantially cell free L-Lysine broth (show at 28 as "Permeate" on the attached figure). The cell rich L-Lysine broth (here treated as retentate waste) is drained off at 32.

(ii) The substantially cell free L-Lysine broth is evaporated to remove water at 36 to produce a substantially cell free concentrated L-Lysine broth 28. Preferably, the substantially cell free concentrated L-Lysine broth (shown as concentrate at 40) has between about 30% and 70% solids by weight. Waste water is drained away at 44.

(iii) The L-Lysine purity of the substantially cell free concentrated L-Lysine broth is adjusted in a mix tank 52. The adjustment is made by adding an L-Lysine containing material at 48 to a mix tank 52 to provide a substantially cell free enriched L-Lysine broth SCFELB at 54. The L-Lysine containing material is added in an amount which brings a final L-Lysine feed supplement with an L-Lysine purity to be in a range theoretically between about 35% and 80% L-Lysine, measured as a percent of free-base per kg, and more preferably between about 50% and 80% L-Lysine.

(iv) The substantially cell free enriched L-Lysine broth is atomized by a nozzle 56 to provide an atomized spray of substantially cell free enriched L-Lysine broth to make a percolating bed of L-Lysine particulates in a spray granulator 60. The L-Lysine particulates have a particle size of less than about 177 micron (i.e. particles that can pass through 80 mesh) and preferably in the size range of about 100 micron and 177 micron. The bed of the spray granulator is preferably a fluidized bed of L-Lysine particulates and is operated at a temperature between about 30° C. and 100° C.

(v) The position of the nozzle 56 is adjusted until it is just above the fluidized bed of L-Lysine particulates.

(vi) Substantially cell free enriched L-Lysine broth is sprayed onto the fluidized bed of L-Lysine particulates to initiate the agglomeration process.

(vii) The agglomeration process is allowed to continue to produce the substantially dust free, free flowing, granular L-Lysine product in the size range between approximately 177 micron and 1190 micron, and preferably in the size range of between about 177 micron to 420 micron.

(viii) The product is removed from the spray granulator at 64, with waste water flowing away at 68 in the form of water vapor in the dryer exhaust.

(ix) The product is then screened and sorted for size at sieve 72 (preferably 80 mesh).

(x) Granules at 76 that are too large (e.g. in the size range of greater than about 1190 micron) are ground in a grinder at 80 to a smaller particle size (e.g. in the size range of less than about 177 micron) and combined with material that is too small 84 (e.g. in the size range of less than about 177 micron) to produce recycled L-Lysine particulates (shown at 88 as "Recharge" on FIG. 1) and returned to the spray granulator 60 as a starting material which act as seeds for the agglomeration process.

(xi) The substantially dust free, free flowing, granular L-Lysine product in the size range of about 177 micron to 1190 micron (shown at 92 as "177–1190 micron Particles") pass through the sieving process and are acceptable as the end product at 96. However, the preferred range is from about 177 micron to 420 micron which packs better and reduces cost for shipment.

The preferred L-lysine concentration in the starting feed stream of L-Lysine fermentation broth is about 90 g/l L-lysine, measured as a percent of free-base per kg. However, the L-lysine concentration can vary from one fermentation run to the next. Hence, the use of a fermentation broth containing about 90 g/l L-Lysine means that other suitable concentrations of L-lysine in the fermentation broth are acceptable. However, the L-Lysine concentration in the fermentation broth should not be below about 30 g/l. As described in step (iii) above, the final desired concentration of L-lysine may be achieved by adding an L-Lysine containing material.

Although ultrafiltration is the preferred method for obtaining the substantially cell free L-Lysine broth, this does not mean other methods can not be used. The cells could also be removed by mechanical separation techniques, such as centrifugation. Other suitable methods include microfiltration and decanting.

The invention envisages the removal of cells from the L-Lysine containing fermentation broth by various other processes. For example, the fermentation broth 20 could be split equally and about 50% centrifuged and the remaining 50% ultrafiltered with the outputs from both cell removal processes combined to produce a substantially cell free L-Lysine broth. This flexibility will enhance the practice of the invention in an industrial setting.

Although the present invention envisages the addition of material containing L-Lysine to the substantially cell free concentrated L-Lysine broth at mix tank 52, the addition of such material to the concentrated L-Lysine broth might be omitted altogether if the desired concentration of L-Lysine (measured as free-base) is such that the addition is unnecessary. For example, the step of adding a material containing L-Lysine might be omitted if the concentration of L-Lysine in the substantially cell free concentrated L-Lysine broth substantially exceeds about 35% L-Lysine, measured as a percent of free-base per kg. If the cell free concentrated L-Lysine broth contains substantially more than about 35% L-Lysine, measured as a percent of free-base per kg, the L-Lysine broth is a substantially cell free enriched L-Lysine broth.

Experience has shown that there is a relationship between the orifice size of the nozzle 56, flow rate, and gauge pressure. While the preferred nozzle size is 0.0615", various other nozzles can also be used to supply the spray. In particular, nozzle designs supplied by Spraying Systems Co., PO Box 7900, Wheaton, Ill. 60189-7900, USA (tel: 630-665-5000) work well to produce a fine spray. The spray granulator can be purchased from Glatt Air Techniques, 20 Spear Road, Ramsey, N.J. 07446-1288, USA (tel: 201-825-8700).

Experience also suggests that manufacturing L-Lysine granules on a commercial scale will require several nozzles to atomize and spray enriched L-Lysine broth onto a proportionally larger bed of percolating particles of L-Lysine.

The percolating bed of particles should comprise L-Lysine particles of sufficiently small size to function as seeds for the agglomeration process. It is preferable that the L-Lysine particulates are less than about 177 micron in size and preferably between about 100 micron and 177 micron.

In the agglomeration process, the seed particles simultaneously grow in size and are dried as they are sprayed with the enriched L-Lysine permeate. The agglomeration process is aided by binders which are inherently present in the enriched L-Lysine broth, namely: L-Lysine fermentation broth, L-Lysine hydrochloride, L-Lysine sulfate and water. A binder is defined as a substance which provides the sticky component to enable the seeds in the agglomeration process to build up in size.

The source of the L-Lysine particulates used to produce and seed the fluidized bed of L-Lysine in the spray granulator is not critical although the preferred source is either obtained from atomizing the substantially cell free enriched L-Lysine broth as described in step (iv) above or from recycled L-Lysine particulates as described in step (x) above, and shown at 88 in FIG. 1.

Alternatively, the fluidized bed of L-Lysine particulates could be produced by either atomizing or spray drying: L-Lysine containing fermentation broth, substantially cell free L-Lysine broth, and substantially cell free concentrated L-Lysine broth or any mixture of these to produce a dry powder of L-Lysine particulates. Another example of a suitable source of the L-Lysine particulates would be dry purified L-Lysine hydrochloride powder and L-Lysine sulfate which has been dried to a powder. The source of L-Lysine particles may be sieved to remove lumps and sorted for particles less than about 177 micron (preferably in the size range between about 100 micron and 177 micron).

Experience has shown that the agglomeration process becomes self-sustaining by using the particles from recycling particles at 88 on either a batch or semi-continuous basis, with batch preferred.

A second embodiment of this invention for producing an L-Lysine feed supplement is shown in FIG. 2.

(i) An L-Lysine containing fermentation broth in a fermenter at 20 is separated into two fractions at 24 to produce a substantially cell free L-Lysine broth (SCFLB 28) and a cell rich L-Lysine broth CRLB 32). The cell rich L-Lysine broth (shown as E2 in FIG. 2) may be processed as described in the third embodiment of FIG. 3. Any suitable means may be used at 24 to separate the amino acid fermentation broth may be used such as ultrafiltration or centrifugation.

(ii) The L-Lysine purity of the substantially cell free L-Lysine broth is adjusted by adding an effective amount of L-Lysine containing material at 48 (FIG. 2) to the substantially cell free L-Lysine broth in a mix tank at 52 in order to provide a substantially cell free enriched L-Lysine broth (SCFELB). The amount of L-Lysine containing material added at 48 depends on the concentration of L-Lysine in the substantially cell free L-Lysine broth, measured as a percent of free-base per kg. However, the amount of L-Lysine should be sufficient to ensure that the final concentration of L-Lysine in the final product is in the range between about 35% and 80% L-Lysine, measured as a percent of free-base per kg.

(iii) The substantially cell free enriched L-Lysine broth is optionally atomized by a nozzle 56 to provide an atomized spray of substantially cell free enriched L-Lysine broth to make a percolating bed of L-Lysine particulates in a spray granulator 60. The L-Lysine particulates have a particle size of less than about 177 micron (i.e. particles that can pass through 80 mesh) and preferably in the size range of about 100 micron and 177 micron. The bed of the spray granulator is preferably a fluidized bed of L-Lysine particulates and is operated at a temperature between about 30° C. and 100° C.

Figure 2A:
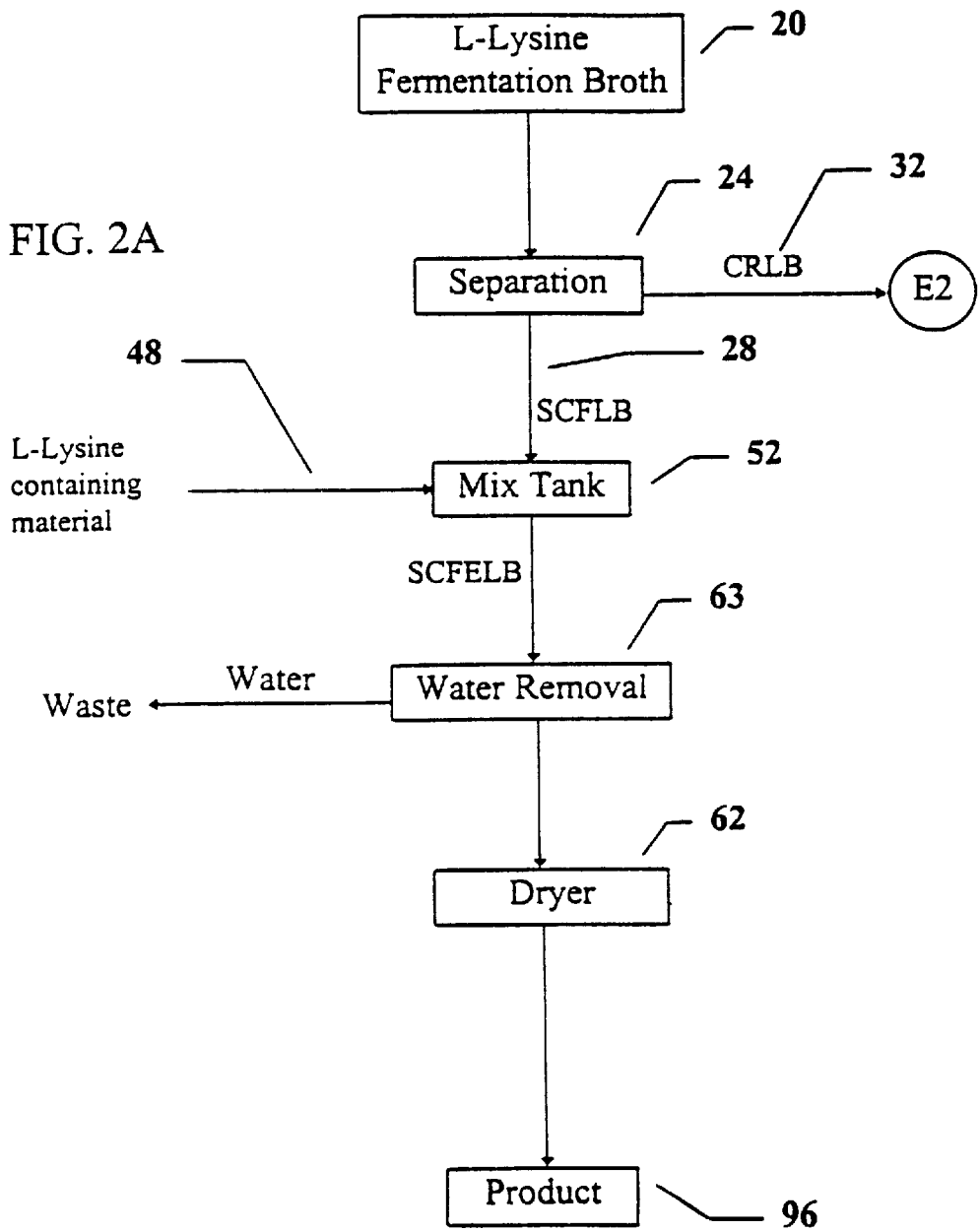
FIG. 2A is a flow chart, showing the principal steps in a process for producing an L-Lysine feed supplement in which a variety of drying means is employed.

Alternatively, the substantially cell free enriched L-Lysine broth of step (ii) in FIG. 2 may be spray dried to provide an L-Lysine feed supplement. An L-Lysine feed supplement may also be produced by tunnel drying, drum drying, rotary drying or tray drying the substantially cell free enriched L-Lysine broth (62 in FIG. 2A). Excess water is removed (63 in FIG. 2A), and preferably by evaporation.

(iv) The position of the nozzle 56 (FIG. 2) is adjusted until it is just above the fluidized bed of L-Lysine particulates of the spray granulator.

(v) Substantially cell free enriched L-Lysine broth is sprayed onto the fluidized bed of L-Lysine particulates of the spray granulator to initiate the agglomeration process.

(vi) The agglomeration process is allowed to continue to produce the substantially dust free, free flowing, granular L-Lysine product in the size range between approximately 177 micron and 1190 micron, and preferably in the size range of between about 177 micron to 420 micron.

(vii) The product is removed from the spray granulator at 64, with waste water flowing away at 68 in the form of water vapor in the spray granulator exhaust.

(viii) The product is then screened and sorted for size at sieve 72 (preferably 80 mesh).

(ix) Granules at 76 that are too large (e.g. in the size range of greater than about 1190 micron) are ground in a grinder at 80 to a smaller particle size (e.g. in the size range of less than about 177 micron) and combined with material that is too small 84 (e.g. in the size range of less than about 177 micron) to produce recycled L-Lysine particulates at 88 (FIG. 2) and returned to the spray granulator 60 as starting material to act as seeds for the agglomeration process.

(x) The substantially dust free, free flowing, "177–1190 micron Particles", granular L-Lysine product with an L-Lysine purity in the range between about 35% and 80% L-Lysine, measured as a percent of free-base per kg, and a size range of about 177 micron to 1190 micron at 92 pass through the sieving process and are acceptable as the end product at 96. However, from the viewpoint of bulk density, the preferred product size is in the range between approximately 177 micron and 420 micron.

A third embodiment (FIG. 3) of this invention produces an L-Lysine feed supplement.

(i) An L-Lysine fermentation broth in fermenter 20 is separated into two fractions at 24 to produce a substantially cell free L-Lysine broth (SCFLB 28) and a cell rich L-Lysine broth (CRLB 32). The substantially cell free L-Lysine broth (shown as E1) may be processed as described in the second embodiment of FIG. 2. Any suitable means to separate the L-Lysine fermentation broth may be used such as ultrafiltration or centrifugation.

Prior to separating the L-Lysine fermentation broth, a material containing L-Lysine may be optionally added directly to the L-Lysine fermentation. The agitation provided by a suitable stirred tank reactor (STR) fermentor vessel would provide the necessary degree of mixing to ensure a uniform concentration of L-Lysine in the L-Lysine fermentation broth.

(ii) The L-Lysine purity of the cell rich L-Lysine broth is adjusted by adding an effective amount of L-Lysine containing material to the cell rich L-Lysine broth in a mix tank at 52 to provide an enriched cell rich broth ECRB 55. The amount of L-Lysine containing material added at 48 depends on the concentration of L-Lysine in the cell rich L-Lysine broth, measured as a percent of free-base per kg. However, the amount should be sufficient to ensure that the final concentration of L-Lysine in the final product is in the range between about 35% and 80% L-Lysine, measured as a percent of free-base per kg.

(iii) Water is removed from the enriched cell rich broth by evaporation at 36 to produce a concentrated cell rich broth CCRB. Preferably, the concentrated cell rich broth has between about 20% and 70% solids by weight.

(iv) The concentrated cell rich broth is dried at 62 to provide an L-Lysine feed supplement 96 with an L-Lysine purity in the range between about 35% and 80% L-Lysine, measured as a percent of free-base per kg.

Alternatively, the concentrated cell rich broth is blended with more L-Lysine containing material in a second mix tank at 104 and then dried at 62. If this embodiment is practiced on a batch or semi-batch basis, it would be more desirable to use just one mix tank (52) simply by recycling the concentrated cell rich broth back at 108 to mix tank 52 as depicted in FIG. 3a.

A fourth embodiment of this invention (FIG. 4) includes a process of producing an L-Lysine feed supplement with an L-Lysine purity in the range between about 35% and 80% L-Lysine, measured as a percent of free-base per kg.

(i) The L-Lysine purity of an L-Lysine fermentation broth in fermenter 20 is adjusted by adding an effective amount of L-Lysine containing material at 48 to a mix tank at 52 in order to provide an enriched L-Lysine fermentation broth ELFB. The amount of L-Lysine containing material added at 48 depends on the concentration of L-Lysine in the L-Lysine fermentation broth, measured as a percent of free-base per kg. However, the amount should be sufficient to ensure that the final concentration of L-Lysine in the final product is in the range between about 35% and 80% L-Lysine, measured as a percent of free-base per kg. Theoretically, it would be beneficial to add L-Lysine free-base at 48 in order to take advantage of the natural aqueous anions present in the L-Lysine fermentation broth. Sulphate, chloride and hydroxyl anions in the L-Lysine fermentation broth would theoretically neutralize the L-Lysine free-base.

(ii) Depending on the position of flow valve 112, the enriched L-Lysine fermentation broth is either converted into a granular L-Lysine feed supplement by means of a spray granulator 60 (i.e. agglomerated) or converted into an L-Lysine feed supplement by means of a spray dryer 61. Water is removed at 63, preferably by evaporation.

Although the present invention envisages the addition of material containing L-Lysine to, for example, L-Lysine containing fermentation broth or concentrated L-Lysine broth. The addition of material containing L-Lysine might be omitted altogether if the desired concentration of L-Lysine (measured as free-base) in the L-Lysine containing fermentation broth or concentrated L-Lysine broth is such that the addition of material containing L-Lysine is unnecessary, as when the concentration exceeds about 35% L-Lysine, measured as a percent of free-base per kg. If the L-Lysine containing fermentation broth or concentrated L-Lysine broth contain substantially more than about 35% L-Lysine, measured as a percent of free-base per kg, then both the broth and concentrate count as enriched L-Lysine broth.

A fifth embodiment of this invention (FIG. 5) includes a process of producing an L-Lysine feed supplement which is essentially the same as that described in the fourth embodiment with the optional step of removing water, preferably by evaporation, from the L-Lysine fermentation broth at 36 in order to provide a concentrated L-Lysine broth with between about 30% and 70% solids by weight. An L-Lysine containing material is added to the concentrated L-Lysine broth at 48 to provide an enriched L-Lysine fermentation broth. The enriched L-Lysine fermentation broth may be spray granulated at 60; spray dried at 61; and spray dried, spray granulated, tunnel dried, tray dried, or drum dried at 62 to provide an L-Lysine feed supplement with an L-Lysine purity in the range between about 35% and 80% L-Lysine, measured as a percent of free-base per kg.

The following examples represent specific but nonlimiting embodiments of the present invention:

EXAMPLE 1

Comparative Example 400 liters of fermentation broth with a L-Lysine concentration of 92 g/l (grams per liter) L-Lysine base and 218 g/l total dry solids were harvested from a L-Lysine fermentation run. This material was ultrafiltered and evaporated to a concentration of 235 g/l in the form of L-Lysine sulfate (measured as free base) and 493 g/l dry solids.

5150 ml (milliliters) of this concentrate was dried on a Glatt WSG 5 spray granulator. The inlet temperature of the Glatt unit was maintained between 93° C. and 124° C., preferably above 120° C. The outlet temperature was maintained between 40° C. and 80° C., preferably between 60 and 65° C. The bed temperature was maintained between 70 to 92° C., preferably between 71 and 74° C. The air flow was maintained between 1,300 and 4,000 feet per minute, preferably between 1,300 and 1,500 feet per minute. The nozzle atomization air was between 50 to 70 pound per square inch gauge. Approximately 2,500 ml of the concentrate was sprayed into the dryer with the nozzle in the highest setting in order to form a bed of material on which to agglomerate. The nozzle was lowered to a position just above the percolating material in the bed and agglomeration was accomplished with the remaining 2,650 ml of concentrate. This yielded a granulated product having the composition indicated in Table 1.

TABLE 1

| Sample | +16 mesh >1190 micron | +40 mesh 420 to 1190 micron | +80 mesh 177 to 420 micron | −80 mesh <177 micron | % Purity* |
|---|---|---|---|---|---|
| Broth | 16.1% | 58.3% | 25.5% | 0% | 46.5% |

*purity measured as percent L-Lysine free-base per kg

EXAMPLE 2

Lysine fermentation broth, ultrafiltered and concentrated as described above in Example 1, was mixed 4 to 1 (lysine basis) with purified L-Lysine sulfate (produced as a free base and pH adjusted to 6 with sulfuric acid yielding L-Lysine sulfate). The mixture was spray granulated as described in Example 1. The process was repeated with a 3 to 2 mixture, 2 to 3 mixture, 1 to 4 mixture, and with straight L-Lysine sulfate. The granulated products had the compositions as indicated in Table 2.

TABLE 2

| Sample | +16 mesh >1190 micron | +40 mesh 420 to 1190 micron | +80 mesh 177 to 420 micron | −80 mesh <177 micron | % Purity* |
|---|---|---|---|---|---|
| 4:1 | 11.6% | 50.9% | 26.1% | 11.4% | 49.0% |
| 3:2 | 28.1% | 17.1% | 49.1% | 5.7% | 52.2% |
| 2:3 | 0.9% | 40.3% | 52.5% | 6.3% | 57.4% |
| 1:4 | 6.1% | 35.0% | 41.8% | 17.1% | 62.5% |
| L-Lysine sulfate | 47.8% | 27.8% | 22.0% | 2.6% | 68.5% |

EXAMPLE 3

Lysine fermentation broth, ultrafiltered and concentrated as described above in Example 1, was mixed 4 to 1 (lysine basis) with pure L-Lysine hydrochloride. The mixture was spray granulated as outlined in Example 1 above. The process was repeated with a 3 to 2 mixture, 2 to 3 mixture, 4 to 1 mixture, and with straight L-Lysine hydrochloride. The granulated products had the compositions as indicated in Table 3.

TABLE 3

| Sample | +16 mesh >1190 micron | +40 mesh 420 to 1190 micron | +80 mesh 177 to 420 micron | −80 mesh <177 micron | % Purity* |
|---|---|---|---|---|---|
| 4:1 | 7.4% | 33.0% | 59.6% | 0% | 49.4% |
| 3:2 | 7.6% | 32.9% | 44.2% | 15.2% | 51.5% |
| 2:3 | 4.8% | 48.4% | 46.8% | 0% | 57.0% |
| 1:4 | 5.1% | 45.3% | 49.4% | 0% | 66.6% |
| L-Lysine HCl | 17.2% | 44.5% | 29% | 9.3% | 76.8% |

It may be seen that mixing the concentrated and ultrafiltered L-Lysine fermentation broth of Example 1 with L-Lysine sulfate or L-Lysine hydrochloride, as described in examples 2 and 3 respectively, produces a granular product with increased L-Lysine content. Also, one preferred embodiment of the described invention enables the L-Lysine content in L-Lysine fermentation broth to be easily adjusted prior to the agglomeration step. Thus, natural variations in L-Lysine concentration, which often occur from one L-Lysine fermentation to the next L-Lysine fermentation, do not require the extensive ion exchange to obtain a final product of the necessary purity for use (e.g. as a feed additive). The preferred level of purity in the final granular L-Lysine product is in the range between about 35% and 80% L-Lysine, measured as a percent free-base per kg.

EXAMPLE 4

Lysine fermentation broth, having a solids content of 193.8 g/kg and a lysine content of 74.3 g/kg is mixed with neutralized L-Lysine produced as free-base to yield a concentration of 508 g/kg lysine and 977.1 g/kg solids.

Approximately 3100 mls of this mixture was dried on a Glatt WSG 5 spray granulator. The inlet temperature was maintained between 136° C. and 146° C. Outlet temperature was maintained between 42° C. and 74° C., preferably between 60° C. and 65° C. Bed temperature was maintained between 63° C. and 79° C., preferably between 71° C. and 74° C. Air flow was maintained between 157 and 209 cubic feet per minute (actual), preferably between 1300 and 1500 feet per minute. Nozzle atomization air was between 50 to 70 pound per square inch gauge. Approximately 2250 ml was sprayed into the dryer with the nozzle in the highest setting in order to form a bed of material on which to agglomerate. The nozzle was lowered to just above the percolating material in the bed and agglomeration was accomplished with the remaining 850 ml of feed. This yielded a granulated product having a purity of 52.0% on a dry basis. The granulated product had the composition as indicated in Table 4.

TABLE 4

| Sample | +16 mesh | +40 mesh | +80 mesh | −80 mesh | % Purity* |
| --- | --- | --- | --- | --- | --- |
| Broth | 8.4% | 38.9% | 43.9% | 8.7% | 52.0% |

*purity measured as percent free-base per kg

EXAMPLE 5

Five kilograms of permeate ultrafiltered from lysine broth, having a purity of 44.9% dry basis and total solids of 69.9 g/kg, was mixed with 182 grams of neutralized L-Lysine, having a purity of 56.3% dry basis and a total solids of 716 g/kg, and spray dried in a Niro Atomizer spray dryer equipped with an atomizing disk type nozzle. The inlet temperature was 230° C., outlet temperature was 80° C., and atomizing disk pressure was 3.3 kp/cm². The feed rate was 34 ml/min. This yielded a product having a purity of 51.2% lysine on a dry basis.

EXAMPLE 6

Five kilograms of permeate ultrafiltered from lysine broth, having a purity of 44.9% dry basis and total solids of 69.9 g/kg, was mixed with 182 grams of neutralized L-Lysine, having a purity of 56.3% dry basis and a total solids of 716 g/kg, and evaporated to 25.4% solids. This evaporated mixture was drum dried. The drum dryer had two counter rotating drums, 8.75" long and 5" in diameter turning at a rate of 2.5 RPM. Steam was supplied to the drum at 40 psi. The feed rate was 20 to 40 ml/min. This yielded a product having a purity of 48.9% lysine on a dry basis.

While the invention is described above in connection with preferred or illustrative embodiments, these embodiments are not intended to be exhaustive or limiting of the invention. Rather, the invention is intended to cover all alternatives, modifications and equivalents included within its spirit and scope of the invention, as defined by the appended claims.

The claimed invention is:

1. A process for producing an L-Lysine feed supplement with an adjustable amount of L-Lysine purity in a range between about 35% and 80% L-Lysine, measured as a percent of free-base per kg, said process comprising the steps of:
    (a) adding a material containing L-Lysine to an L-Lysine fermentation broth to provide an enriched L-Lysine fermentation broth, said added material being an amount which brings a final L-Lysine feed supplement with an L-Lysine purity within a range between about 35% and 80% L-Lysine, measured as a percent of free-base per kg; and
    (b) substantially drying the enriched L-Lysine fermentation broth of step (a) to provide said final L-Lysine feed supplement.

2. The process of claim 1 wherein the L-Lysine feed supplement of step (b) has between about 50% and 80% L-Lysine, measured as a percent of free-base per kg.

3. The process of claim 1 wherein the material containing L-Lysine of step (a) is selected from a group consisting of L-Lysine hydrochloride, L-Lysine sulfate, and neutralized L-Lysine.

4. The process of claim 1 wherein the material containing L-Lysine of step (a) is L-Lysine free-base.

5. The process of claim 1 wherein the substantial drying of step (b) is carried out in a dryer selected from a group consisting essentially of: drum drying, spray drying, rotary drying, tray drying, tunnel drying, and spray granulation.

6. A process for producing an L-Lysine feed supplement with an adjustable amount of L-Lysine purity in a range between about 35% and 80% L-Lysine, measured as a percent of free-base per kg, comprising the steps of:
    (a) removing water from an L-Lysine fermentation broth to provide a concentrated L-Lysine broth;
    (b) adding a material containing L-Lysine to said concentrated L-Lysine broth of step (a) to provide an enriched L-Lysine fermentation broth, said added material being an amount which brings a final L-Lysine feed supplement with an L-Lysine purity into a range between about 35% and 80% L-Lysine, measured as a percent of free-base per kg; and
    (c) substantially drying the enriched L-Lysine fermentation broth of step (b) to provide the final L-Lysine feed supplement.

7. The process of claim 6 wherein the concentrated L-Lysine broth of step (a) has between about 30% and 70% solids by weight.

8. The process of claim 6 wherein the material containing L-Lysine of step (b) is selected from a group consisting of L-Lysine hydrochloride, L-Lysine sulfate, and neutralized L-Lysine.

9. The process of claim 6 wherein step (a) comprises evaporating the L-Lysine fermentation broth to remove water in order to provide said concentrated L-Lysine broth.

10. The process of claim 7 wherein the evaporation of step (a) is carried out between about 140° F. and 214° F.

11. The process of claim 7 wherein the evaporation of step (a) is carried out between about 145° F. and 155° F.

12. The process of claim 7 wherein the evaporation of step (a) is carried out in a vacuum between about 2.9 psia and 11 psia.

13. The process of claim 7 wherein the evaporation of step (a) is carried out in a vacuum between about 2.9 psia to 4 psia.

14. The process of claim 6 wherein the enriched L-Lysine fermentation broth of step (b) has between about 50% and 80% L-Lysine, measured as a percent of free-base per kg.

15. The process of claim 6 wherein the substantial drying of step (c) is selected from a group consisting essentially of: drum drying, spray drying, tray drying, tunnel drying, rotary drying, and spray granulation.

16. A process for producing an L-Lysine feed supplement with an adjustable amount of L-Lysine purity in a range between about 35% and 80% L-Lysine, measured as a percent of free-base per kg, comprising the steps of:

(a) separating an L-Lysine fermentation broth into substantially cell free L-Lysine broth and cell rich L-Lysine broth;

(b) adding a material containing L-Lysine to said cell rich L-Lysine broth of step (a) to provide an enriched cell rich broth, said added material is an amount which brings a final L-Lysine feed supplement with an L-Lysine purity into a range between about 35% and 80% L-Lysine, measured as a percent of free-base per kg;

(c) removing water from said enriched cell rich broth of step (b) to provide a concentrated cell rich broth; and (d) drying said concentrated cell rich broth of step (c) to provide the final L-Lysine feed supplement.

17. The process according to claim 16 wherein step (c) further comprises adding an additional amount of material containing L-Lysine to said concentrated cell rich broth.

18. The process according to claim 16 wherein drying means of step (d) is is selected from a group consisting essentially of a tunnel dryer, drum dryer, rotary dryer, and a tray dryer.

19. A process for producing an L-Lysine feed supplement with an adjustable amount of L-Lysine purity in a range between about 35% and 80% L-Lysine, measured as a percent of free-base per kg, comprising the steps of:

(a) separating an L-Lysine fermentation broth into substantially cell free L-Lysine broth and cell rich L-Lysine broth;

(b) adding a material containing L-Lysine to said substantially cell free L-Lysine broth of step (a) to provide a substantially cell free enriched L-Lysine broth, said added material being an amount which brings a final L-Lysine feed supplement with an L-Lysine purity into a range between about 35% and 80% L-Lysine, measured as a percent of free-base per kg; and (c) drying said substantially cell free enriched L-Lysine broth of step (b) to provide the final L-Lysine feed supplement.

20. The process according to claim 19 wherein drying means of step (c) is selected from a group consisting essentially of: a spray granulator, spray dryer, tunnel dryer, drum dryer, rotary dryer, and a tray dryer.

21. The process according to claim 19 wherein step (c) further comprises a sieving step to select particles in the size range between about 177 micron and 1190 micron.

22. A process for producing an L-Lysine feed supplement with an adjustable amount of L-Lysine purity in a range between about 35% and 80% L-Lysine, measured as a percent of free-base per kg, comprising the steps of:

(a) removing water from an L-Lysine containing fermentation broth to provide a concentrated L-Lysine broth;

(b) determining the concentration of L-Lysine, measured as a percent of free-base per kg, in the concentrated L-Lysine broth;

(c) adding a material containing L-Lysine to the concentrated L-Lysine broth to provide an enriched L-Lysine broth if the concentration of L-Lysine in the concentrated L-Lysine broth, measured as a percent of free-base per kg, is below about 35%, said added material being an amount which brings a final L-Lysine feed supplement with an L-Lysine purity into a range between about 35% and 80% L-Lysine, measured as a percent of free-base per kg; and (d) substantially drying the enriched L-Lysine broth to provide the final L-Lysine feed supplement.

23. A process for producing an L-Lysine feed supplement with an adjustable amount of L-Lysine purity in a range between about 35% and 80% L-Lysine, measured as a percent of free-base per kg, comprising the steps of:

(a) removing water from an L-Lysine containing fermentation broth by evaporating the L-Lysine containing fermentation broth in a temperature range of about 140° F. and 214° F. and in a vacuum out between about 2.9 psia and 11 psia to provide a concentrated L-Lysine broth which is between about 30% and 70% solids by weight;

(b) determining the concentration of L-Lysine, measured as a percent of free-base per kg, in the concentrated L-Lysine broth;

(c) adding a sufficient amount of material containing L-Lysine to said concentrated L-Lysine broth to provide an enriched L-Lysine broth if the concentration of L-Lysine in the concentrated L-Lysine broth, measured as a percent of free-base per kg, is below about 35%, said added material containing L-Lysine being selected from a group consisting of L-Lysine hydrochloride, L-Lysine sulfate, and neutralized L-Lysine, said added material being an amount which brings a final L-Lysine feed supplement with an L-Lysine purity into a range between about 35% and 80% L-Lysine, measured as a percent of free-base per kg; and (d) substantially drying the enriched L-Lysine broth to provide the final L-Lysine feed supplement with an L-Lysine purity into a range between about 35% and 80% L-Lysine, measured as a percent of free-base per kg.

24. A process for producing an L-Lysine feed supplement comprising:

(a) determining the concentration of L-Lysine, measured as a percent of free-base per kg, in an L-Lysine containing fermentation broth;

(b) adding a material containing L-Lysine to the L-Lysine containing fermentation broth to provide an enriched L-Lysine broth, said added material being an amount which brings a final L-Lysine feed supplement with an L-Lysine purity into a range between about 35% and 80% L-Lysine, measured as a percent of free-base per kg, said added material containing L-Lysine being selected from a group consisting essentially of L-Lysine hydrochloride, L-Lysine sulfate, and neutralized L-Lysine; and (c) substantially drying the enriched L-Lysine broth to provide the final L-Lysine feed supplement.

* * * * *